US011445742B2

(12) United States Patent
Sand et al.

(10) Patent No.: US 11,445,742 B2
(45) Date of Patent: Sep. 20, 2022

(54) COATED EGG YOLK CORES, METHODS OF MAKING AND METHODS OF USE THEREOF

(71) Applicant: WISCONSIN ALUMNI RESEARCH FOUNDATION, Madison, WI (US)

(72) Inventors: Jordan Marshall Sand, Verona, WI (US); Mark Eric Cook, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/110,585

(22) Filed: Dec. 3, 2020

(65) Prior Publication Data

US 2021/0084962 A1 Mar. 25, 2021

Related U.S. Application Data

(62) Division of application No. 15/673,893, filed on Aug. 10, 2017, now Pat. No. 10,881,129.

(51) Int. Cl.
| | | |
|---|---|---|
| *A23P 20/10* | (2016.01) | |
| *A61K 39/44* | (2006.01) | |
| *A23K 40/30* | (2016.01) | |
| *A61K 39/395* | (2006.01) | |
| *C07K 16/24* | (2006.01) | |
| *A23P 20/18* | (2016.01) | |
| *C07K 16/02* | (2006.01) | |

(52) U.S. Cl.
CPC ............. *A23P 20/10* (2016.08); *A23K 40/30* (2016.05); *A23P 20/18* (2016.08); *A61K 39/39591* (2013.01); *A61K 39/44* (2013.01); *C07K 16/02* (2013.01); *C07K 16/248* (2013.01); *A23V 2200/30* (2013.01); *C07K 2317/11* (2013.01); *C07K 2317/23* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway et al. |
| 9,505,836 B2 | 11/2016 | Sand et al. |
| 2009/0263561 A1 | 10/2009 | Machpherson et al. |
| 2011/0008362 A1 | 1/2011 | Sunwoo et al. |
| 2011/0159002 A1 | 6/2011 | Du Bourdieu et al. |
| 2015/0037277 A1 | 2/2015 | Cook et al. |
| 2019/0045830 A1 | 2/2019 | Sand et al. |

FOREIGN PATENT DOCUMENTS

| | | |
|---|---|---|
| AU | 2012244263 A1 | 11/2012 |
| CA | 723608 A | 12/1965 |
| WO | 2008086621 A1 | 7/2008 |

OTHER PUBLICATIONS

Abe et al.; "Design of Enzyme-Encapulated Protein Containers by In Vivo Crystal Engineering"; Adv. Mater., 27; pp. 7951-7954; (2015).
Akkouche et al.; "Effect of Heat on Egg White Proteins"; International Conference on Applied Life Sciences (ICALS2012), pp. 407-413; Turkey, Sep. 10-12, 2010.
Arendt et al.; "Interleukin-10 Neutralizing Antibody for Detection of Intestinal Luminal Levels and as a Dietary Additive in Eimeria Challenged Broiler Chicks"; Poultry Science;95; pp. 430-438 (2016).
Chalghoumi et al.; "Hen Egg Yolk Antibodies (IgY), Production and Use for Passive Immunization Against Bacterial Enteric Infections in Chicken: a Review"; Biotechnol. Agron. Soc. Environ.; 13(2); pp. 295-308; (2009).
Cutlip et al.; "The Effect of Steam-Conditioning Practices on Pellet Quality and Growing Broiler Nutritional Value"; J. Appl. Poult. Res.; 17; pp. 249-261; (2008).
De Jong, Joan A. H., "Properly Determine Powder Flowability to Maximize Plant Output"; Chemical Engineering Progress; 95(4); pp. 25-34; (1999).
Dziezak, Judie D., K "Microencapsulation and Encapsulated Ingredients"; Food Technology; Apr.; pp. 136-152; (1988).
Friedrich, I.; Glatt "Test Report"; Project No. 94820, Trial V003-17/17-018 for Ab E Discovery; Egg York and Egg White; 3 pages; 2017-05-08_treport_94820_17-018.docx.
Gibbs et al.; "Encapsulation in the Food Industry: a Review"; International Journal of Food Sciences and Nutrition; 50; pp. 213-224; (1999).
International Search Report and Written Opinion; International Application No. PCTUS2018/043007; International Filing Date Jul. 20, 2018; dated Oct. 5, 2018; 16 pages.
IsoNova [online]; [retrieved on Feb. 12, 2020]; retrieved from the Internet https://www.isonovatech.com/egg-albumin-protein/ IsoNova Contributor; "Egg Albumin Protein"; IsoNova; 2020; 3 pages.
Iwashita et al.; "Thermal Aggregation of Hen Egg White Proteins in the Presence of Salts"; The Protein Journal, vol. 34, Issue No. 3; 2015; pp. 212-219.
Karaca et al.; "Encapsulation of Flaxseed Oil Using a Benchtop Spray Dryer for Legume Protein—Maltodextrin Microcapsule Preparation"; Journal of Agricultural and Food Chemistry; 61; pp. 5148-5155; (2013).
Koga et al.; "Stability of Trans-Resveratrol Encapsulated in a Protein Matrix Produced Using Spray Drying to UV Light Stress and Simulated Gastro-Intestinal Digestion"; Journal of Food Science; 81(2); pp. C291-C300; (2016).
Lilavivat et al.; "In Vivo Encapsulation of Nucleic Acids Using an Engineered Nonviral Protein Capsid"; J. Am. Chem. Soc. 134; pp. 13152-13155; (2012).

(Continued)

*Primary Examiner* — Benjamin P Blumel
(74) *Attorney, Agent, or Firm* — Cantor Colburn LLP

(57) ABSTRACT

A method of making coated avian egg yolk cores includes providing dried avian egg yolk cores having a diameter of 100 to 1500 micrometers, applying avian egg albumen to the dried avian egg yolk cores to provide the coated avian egg yolk cores, and optionally drying the coated avian egg yolk cores, wherein the ratio of dry avian egg albumen to dried avian egg yolk in the coated avian egg yolk cores is 1:10 to 10:1. Also included are the coated avian egg yolk cores, food and feed additives containing the coated avian egg yolk cores and food and feed compositions containing the coated avian egg yolk cores.

15 Claims, 2 Drawing Sheets

(56) References Cited

OTHER PUBLICATIONS

Luzzi, Louis A.; "Review Article—Microencapsulation"; Journal of Pharmaceutical Sciences; 59(10); pp. 1367-1376; (1970).
MaHam et al.; "Protein-Based Nanomedicine Platforms for Drug Delivery"; Small; 5(15); pp. 1706-1721; (2009).
Muthuselvi et al; "Simple Coacervates of Zein to Encapsulate Gitoxin"; Colloids and Surfaces B: Biointerfaces; 51; pp. 39-43; (2006).
Sand et al.; "Oral Antibody to Interleukin-10 Reduces Growth Rate Depression Due to Eimeria Spp. Infection in Broiler Chickens"; Poultry Science; 95; pp. 439-446; (2016).
Shahidi et al.; "Encapsulation of Food Ingredients"; Critical Reviews in Food Science and Nutrition; 33(6); pp. 501-547; (1993).
Tavares et al.; "Milk Proteins as Encapsulation Devices and Delivery Vehicles: Applications and Trends"; Trends in Food Science & Technology; 37; pp. 5-20; (2014).
Van Der Plancken et al; "Heat-induced Changes in the Susceptibility of Egg White Proteins to Enzymatic Hydrolysis: a Kinetic Study"; J. Agric. Food Chem.; 51; pp. 3819-3823; (2003).
Weinbreck et al.; "Microencapsulation of Oils Using Whey Protein/Gum Arabic Coacervates"; J. Microencapsulation; 21(6); pp. 667-679; (2004).
Xinde et al.; "Measurement and Influence Factors of the Flowability of Microcapsules with High-Content Beta-Carotene"; Chin J. Chem. Eng.; 14(4); pp. 579-585; (2007).

COATED EGG YOLK CORES, METHODS OF MAKING AND METHODS OF USE THEREOF

CROSS-REFERENCE TO RELATED APPLICATIONS

This application is a divisional of U.S. application Ser. No. 15/673,893 filed on Aug. 10, 2017, which is incorporated herein by reference in its entirety.

FIELD OF THE DISCLOSURE

The present disclosure is related to coated avian egg yolk cores, particularly those avian egg yolk cores containing IgY antibodies or other peptides, particularly coated avian egg yolk cores that can withstand conditions of heat and steam used in food processing.

BACKGROUND

Avian eggs, specifically from domestic chickens, have been used to produce antibodies, referred to herein as egg antibodies. There are some advantages to using egg antibodies, which include lower background cross-reactions with research samples. Egg antibodies are known as IgY.

IgY as a single class of antibody is present in only the egg yolk, while mammalian antibody classes are all mixed together in serum. The natural segregation of a single antibody class in the egg yolk makes isolation of the single antibody easy in comparison to processing serum to obtain a single mammalian antibody class. Chicken IgY antibodies may be freeze dried with little or no loss in functionality. Production of egg antibodies from chicken eggs is inherently safe. Eggs are generally recognized as safe, and isolating IgY antibodies from egg yolk involved neither needles nor hazardous chemicals.

Egg antibodies have been used to treat a wide variety of bacterial, viral and protozoal diseases. However, widespread adoption of these technologies has been hampered by the sensitivity of egg antibodies to heat and steam treatment.

What is needed are methods of preparing egg antibodies in their natural and safe composition so that they are stable to harsh conditions such as heat and steam.

BRIEF SUMMARY

In one aspect, a method of making coated avian egg yolk cores comprises providing dried avian egg yolk cores having a diameter of 100 to 1500 micrometers, applying avian egg albumen to the dried avian egg yolk cores to provide the coated avian egg yolk cores, and optionally drying the coated avian egg yolk cores, wherein the ratio of dry avian egg albumen to dry avian egg yolk in the coated avian egg yolk cores is 1:10 to 10:1.

In another aspect, a food or feed composition comprises a basal food or feed composition and the coated avian egg yolk cores made by the foregoing method.

In yet another aspect, a food or feed composition comprises a basal food composition and coated avian egg yolk cores comprising an avian egg albumen coating, wherein the avian egg yolk cores have a diameter of 100 to 1500 micrometers, and the ratio of dry avian egg albumen to dry avian egg yolk in the coated avian egg yolk cores is 1:10 to 10:1.

In a further aspect, a food or feed additive composition comprises the coated avian egg yolk cores made by the foregoing method.

In another aspect, a food or feed additive composition comprises a carrier and coated avian egg yolk cores comprising an avian egg albumen coating, wherein the avian egg yolk cores have a diameter of 100 to 1500 micrometers, and the ratio of dry avian egg albumen to dry avian egg yolk in the coated avian egg yolk cores is 1:10 to 10:1.

In a yet further aspect, a composition comprises coated avian egg yolk cores comprising an egg albumen coating, wherein the avian egg yolk cores have a diameter of 100 to 1500 micrometers, and wherein the ratio of dry avian egg albumen to dry avian egg yolk in the coated avian egg yolk cores is 1:10 to 10:1.

Figure 1:
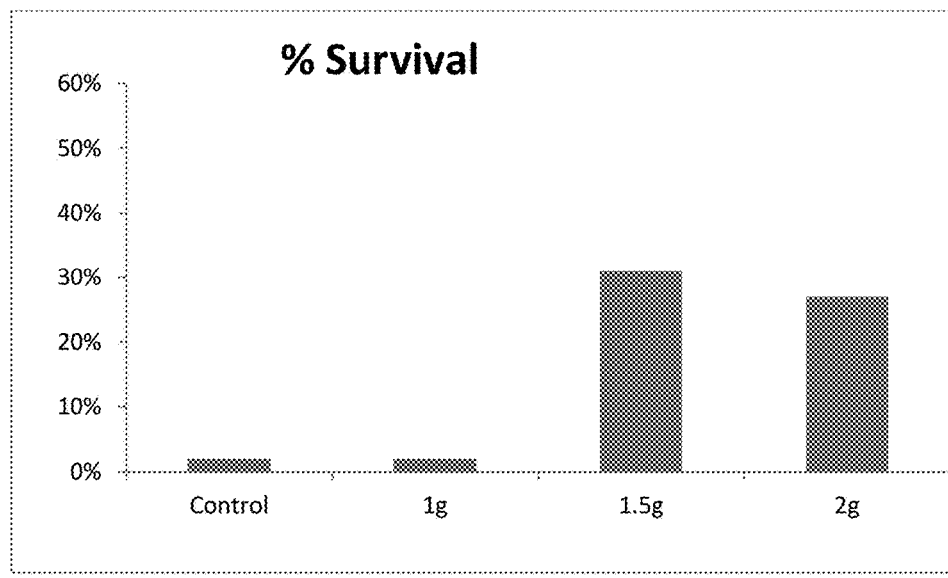
FIG. 1 shows the percentage of antibody activity for an uncoated egg yolk (control) compared to 1, 1.5, and 2 g of egg albumen coated onto 2 g of egg yolk following the treatment with steam for 1 minute 30 seconds

The above-described and other features will be appreciated and understood by those skilled in the art from the following detailed description, drawings, and appended claims.

DETAILED DESCRIPTION

As described, for example, in U.S. Pat. No. 9,505,836, anti-Il-10 antibodies such as avian egg yolk antibodies can be added to animal feeds such as chicken feeds to reduce the incidence of Coccidiosis. However, the production of chicken feed pellets, for example, typically involves the use of both heat and steam, e.g., temperatures of up to 93° C. and a steam pressure of 552 kPa. It has been unexpectedly found that coating dried avian egg yolk cores with avian egg albumen protects the egg yolk antibodies from heat and steam. It is expected that the coatings and methods described herein can be used to protect egg yolks, particularly egg yolks including any bioactive polypeptide.

In an aspect, a method of making coated avian egg yolk cores comprises providing dried avian egg yolk cores having a diameter of 100 to 1500 micrometers, applying avian egg albumen to dried avian egg yolk cores to provide the coated avian egg yolk cores, and optionally drying the coated avian egg yolk cores, wherein the ratio of dry avian egg albumen to dry avian egg yolk in the coated avian egg yolk cores is 1:10 to 10:1.

Egg yolk may be isolated from eggs and dried by spray or refractant drying methods prior to forming egg yolk cores.

Dried avian egg yolk cores are prepared using standard methods for making cores such as granulation and micronization. Wet granulation or dry granulation techniques may be employed. It is preferred that the egg yolk cores have a diameter of 100 to 1500 micrometers, although other diameters may be employed. In an aspect, the water content of the dried avian egg yolk cores is less than 5 wt % of the total weight of the dried avian egg yolk cores.

Coating of the avian egg yolk cores with avian egg albumen can be done by applying liquid avian egg albumen to the dried avian egg yolk cores. In an aspect, the liquid avian egg albumen comprises 50-90 wt % water. Exemplary coating methods include fluidized bed coating, spraying, top spray coating, bottom spray coating, or pan coating. Coating of the avian egg yolk cores with avian egg albumen can also be done using dry avian egg albumen and dry coating techniques such as powder coating.

In an aspect, the avian egg albumen core substantially completely covers the avian egg yolk cores to provide a shell on the exterior of the cores.

The dried avian egg yolk cores optionally include a bioactive polypeptide. Exemplary bioactive polypeptides include enzymes, cytokines, antibodies, hormones, growth factors, or a combination comprising at least one of the foregoing bioactive polypeptides. In an aspect, the bioactive polypeptide is heat labile.

In an aspect, the bioactive polypeptide is released from the coated cores. For example, wherein the coated cores have a dissolution profile when tested in a U.S.P. Type II dissolution apparatus at 37° C. and 50 rpm, in pH 6.8 buffer as follows: at 5 minutes greater than or equal to about 5% of the bioactive polypeptide is released In an alternative embodiment, release of the bioactive polypeptide can be determined by treating the coated cores with a 2-fold volume of aqueous solution (pH 5) for 5 minutes, and measuring the activity of the bioactive polypeptide. For example, when the bioactive polypeptide is an antibody, the activity can be measured by detecting binding of the antibody to an immunogenic polypeptide for the antibody.

In a specific aspect, the bioactive peptide is an IgY antibody, for example, an IgY antibody was transferred to the egg yolk in response to immunization of the avian with an immunogenic polypeptide. Preferably, the IgY antibody specifically binds the immunogenic polypeptide.

To produce avian egg yolk antibodies, for example, an immunogenic polypeptide is injected into laying fowl, such as hens, preferably at various intervals, to induce an immune response. The hens may be injected intramuscularly or subcutaneously. The specific mode of injection is not essential. It is well known that the IgY antibodies produced by the hens in response to such an immune challenge are transferred and concentrated in the egg yolk.

Once the eggs are harvested, the eggs may be further processed to isolate the egg yolk, which itself may be further processed. The egg yolk may be dried by spray or refractant drying methods.

In a specific embodiment, the yolk is separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. The collected egg yolk may be diluted with an aqueous buffer solution or distilled water in a ratio of about 1:2 to about 1:40 v/v, and more specifically, in a ratio of about 1:5 to about 1:30 v/v. For efficient recovery of yolk antibodies, pH is about 5-7. Desirably, the temperature in this step is within about 0° C. to about 60° C.

In one embodiment, the egg yolk including the antibodies are further dried to form a powder including the antibodies.

The whole egg, egg yolk or parts of the egg may be spray dried. Spray drying may be performed using known spray drying methods and commercially available spray drying equipment. Dry egg powders may also be prepared by lyophilization. The dry egg powders can then be used to form the dried avian egg yolk cores In an aspect, the IgY antibody in the coated avian egg yolk cores loses less than 10, 20, 30, 40, 50, 60, 70 80 or 90% of its bioactivity when exposed to temperatures of up to 93° C. and a steam pressure of 552 kPa for 3 minutes or less. Bioactivity can be measured as binding of the IgY antibody to an immunogenic polypeptide.

In any of the foregoing aspects, the coated avian egg yolk cores have a flow factor of greater than 4, a Hausner ratio of 1-1.25, a static angle of repose of less than 60, or a combination thereof.

The primary measure of powder flowability is the powder flow function which provides a measure of the amount of strength the material retains at a stress free surface following consolidation to a given stress level. The flow factor can be measured using a uniaxial unconfined failure test in which powder is placed in a cylindrical cell and compressed. The sample is then unmolded to provide a compacted column of powder. The stress on the column of powder is increased until failure occurs and the peak normal stress is recorded. The uniaxial unconfined failure test is conducted over a range of consolidation stresses and the flow function is constructed by plotting the unconfined failure strength versus the consolidation stress. The greater the flow factor (ff) value, the more free-flowing the powder (Table 1).

TABLE 1

Standard Classification of Powder Flowability

| Classification | Flow Factor (FF) |
| --- | --- |
| Non-flowing | <1 |
| Very cohesive | 1-4 |
| Cohesive | 2-4 |
| Easy flowing | 4-10 |
| Free flowing | >10 |

The Hausner ratio is based upon a comparison of the "as poured" and tapped bulk density. The Hausner ratio is $V°/Vf$, wherein $V°$ is the unsettled volume and $Vf$ is the tapped volume after tapping the material until no further volume changes occur. The Hausner ratio can be determined using a 250 mL volumetric cylinder with a test weight of 100 g, for example.

The static angle of repose is related to the interparticulate friction or resistance to movement between particles. The angle of repose is determine by forming a symmetrical cone of powder on a fixed diameter base. The angle of repose is determined by measuring the height of the cone of powder and calculating the angle of repose (a) using the formula:

$$Tan(\alpha) = height/(0.5 base).$$

The present disclosure is further generally directed to food or feed additives including the coated avian egg yolk cores described herein, for example made by the methods described herein. The food or feed additives optionally include a carrier.

In an aspect, a food or feed additive composition comprises a carrier and coated avian egg yolk cores comprising an avian egg albumen coating, wherein the avian egg yolk cores have a diameter of 100 to 1500 micrometers, and the ratio of dry avian egg albumen to dry avian egg yolk in the coated avian egg yolk cores is 1:10 to 10:1.

As used herein, a food or feed additive is a substance that is added to food or feed to enhance the properties of the food or feed.

In an aspect, a food or feed composition comprises a basal food or feed composition and the coated avian egg yolk cores made by the methods described herein.

In another aspect, a food or feed composition comprises a basal food composition and coated avian egg yolk cores comprising an avian egg albumen coating, wherein the coated avian egg yolk cores have a diameter of 100 to 1500 micrometers, and the ratio of dry avian egg albumen to dry avian egg yolk in the coated avian egg yolk cores is 1:10 to 10:1.

As used herein, the term "feed" broadly refers to a material, liquid or solid, that is used for nourishing an animal, and for sustaining normal or accelerated growth of an animal including newborns or young and developing animals. The term includes a compound, preparation, mixture, or composition suitable for intake by an animal. Specifically, the feed is suitable for poultry such as quail, ducks, turkeys, and chickens. A feed composition comprises a basal feed composition. The term "basal feed composition" refers to a feed composition combinable with additives such as the coated egg yolk cores described herein. Basal animal feed compositions may include components such as proteins, grains, flavor compositions, vitamins, minerals, preservatives, and the like. Basal feed compositions can be suitable for ingestion by a target animal.

An animal feed may further include optional ingredients including vitamins, minerals, antibiotics, lipids, carbohydrates, proteins, antioxidants, and amino acids.

Exemplary vitamins include Vitamin A, Vitamin B, Vitamin D, Vitamin E, and Vitamin K. Exemplary minerals include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Exemplary antibiotics include penicillin, streptomycin, tetracyclines, zinc bacitracin and aureomycin.

Exemplary lipids include oil seeds, oils and lipids derived from plants or animals. Sources of oilseeds, oils and lipids include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Exemplary carbohydrates include starch, cellulose, pentosans, other complex carbohydrates, corn, milo, barley, rye, oats, wheat, wheat middlings, and various grain-by-products.

Exemplary sources of protein include protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Exemplary amino acids include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Exemplary antioxidants include beta-carotene, Vitamin E, Vitamin C, and tocopherol, or synthetic antioxidants.

Specifically, the animal feed including the coated avian egg yolk cores is a feed for avian species such as quail, ducks, turkeys, and chickens, as well as feeds for mammals including swine, cows, dogs, cats, rabbits and the like. The coated avian egg yolk cores are particularly useful in pelleted feeds.

As used herein, the term "food" broadly refers to a material, liquid or solid, that is used for nourishing a human. The term includes a compound, preparation, mixture, or composition suitable for intake by humans. A food composition comprises a basal food composition. The term "basal food composition" refers to a food composition combinable with additives such as the coated egg yolk cores described herein.

Exemplary basal food compositions include milk, juice, formula, and solid foods such as snack food consumable by humans including human children.

As used herein, an egg product is defined as a product that is free of shells or other non-egg material which might occur unavoidably in good processing practice, and contains a maximum ash content of 6% on a dry matter basis.

In another aspect, a composition comprises coated avian egg yolk cores comprising an egg albumen coating, wherein the avian egg yolk cores have a diameter of 100 to 1500 micrometers, wherein the ratio of dry avian egg albumen to dry avian egg yolk in the coated avian egg yolk cores is 1:10 to 10:1.

The invention is further illustrated by the following non-limiting examples.

EXAMPLES

Methods

Example 1: An Egg Albumen Coating Protects Dried Egg Yolk Cores in a Steam Environment Egg yolks containing an anti-Il-10 antibody were separated from the white and dried at 65° C. for 14 hours to provide egg yolk having a water content of less than 5 wt % based on the total weight of the egg yolk. The dried egg yolk was granulated to provide egg yolk cores having diameters of 400 to 1200 microns, with an average diameter of 800 microns measured by an optical image analysis system (Camsizer-Retsch). Alternatively, the diameter of the egg yolk cores can be determined by microscopic analysis, or by passing through screens with holes of known diameter.

Egg yolks contain both an oil phase and an aqueous phase. Because the IgY antibodies in egg yolk, for example, are found in the aqueous phase, during the coating process, the antibodies migrate from the yolk to the egg albumen coating during laboratory-scale coating if the albumen coating was too high in moisture or the drying process was not rapid (instantaneous). In order to ensure that the antibody remained in the yolk, egg albumen was dialyzed against Drierite™ overnight to reduce the water content and thus reduce the chance of the antibody migrating to the outside of the sphere. Natural egg albumen has a water content of about 90% by weight, and for these experiments, the water content was reduced to about 50% by weight of the total weight of the egg albumen.

In these experiments, 2 grams of egg yolk cores was overlaid with either 0 grams (control), 0.85 grams, 1.5 grams, 1.75 grams, 3 grams, 3.5 grams or 4 grams of egg albumen to provide egg yolk cores coated with different amount of egg albumen and dried at 65 C for 14 hours. The ratio of 1.75 g of dry egg albumen:2 g of dry egg yolk corresponds to the natural ratio of albumen:yolk. The coated egg yolk cores were dried in an oven at 65° C. for 14 hours. Then 0.2 g of each batch of cores mixed with 3.8 g chicken mash (or pre-pelleted chicken feed) and exposed to 90 seconds of steam at 210° F.

IgY activity was determined by ELISA using an IL-10 peptide-ovalbumin conjugate. ELISA plates were prepared by diluting 100 μL of IL-10 peptide conjugate in 12.5 mL coating buffer and using 100 μL/well in a Costar 96 well plate. The plates were sealed and incubated overnight and up to 3 days at 4° C.

Samples were prepared by weighing out 4 g (±0.05 g) of each sample into 15 mL conical centrifugation tubes, adding 6 mL of PBS to each sample tube and vortexing for 30 seconds. The samples were incubated overnight at 4° C. Samples were held at room temperature for 1 hour and then centrifuged at 3,000 g (3,625 rpm) for 20 min at 4° C. Using the supernatant only, a 1:32 dilution was made. For the positive control (no heat/steam treatment), for example, a two-fold dilution series was made. An example of a positive control dilution series is provided below:

i. A 7, 8, 9 (1:20)
ii. B 7, 8 9 (1:40)
iii. C 7, 8, 9 (1:80)
iv. D 7, 8, 9 (1:160)
v. E 7, 8, 9 (1:320)
vi. D 7, 8, 9 (1:640)
vii. F 7, 8, 9 (1:1280)
viii. G 7, 8, 9 (1:2560)

Figure 2:
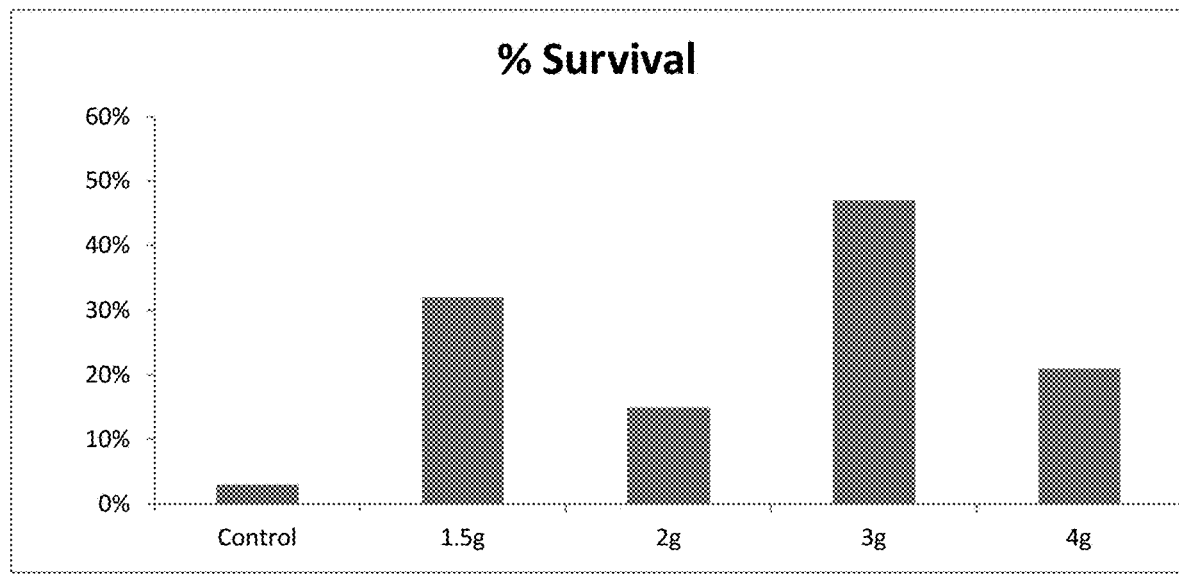
FIG. 2 shows the percentage of antibody activity for an uncoated egg yolk (control) compared to 1.5, 2, 3 and 4 g of egg albumen coated onto 2 g of egg yolk following the treatment with steam for 1 minute 30 seconds.
Figure 3:
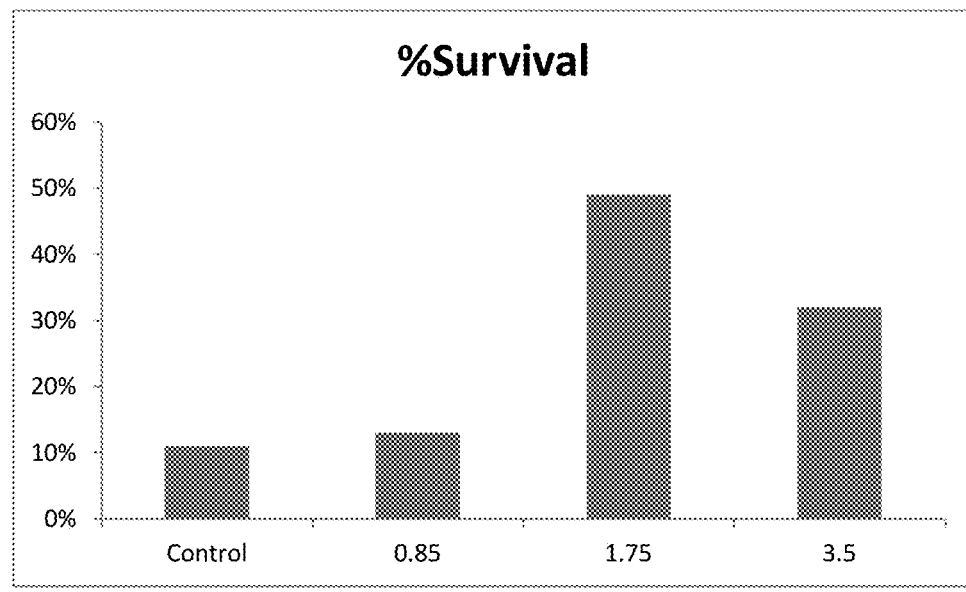
FIG. 3 shows the percentage of antibody activity for an uncoated egg yolk (control) compared to 0.85, 1.75, and 3.5 g of egg albumen coated onto 2 g of egg yolk following the treatment with steam for 1 minute 30 seconds.
Figure 4:
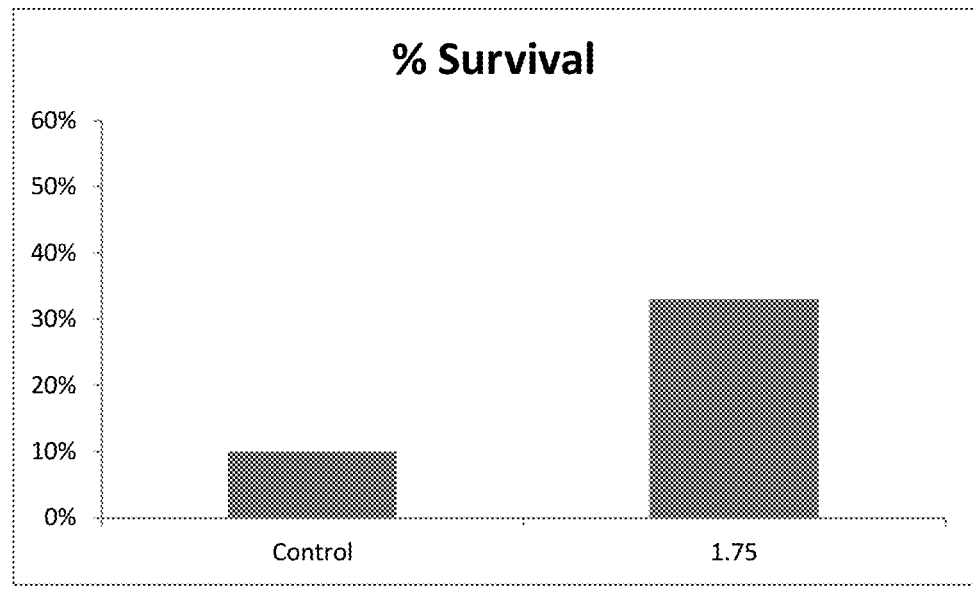
FIG. 4 shows the percentage of antibody activity for an uncoated egg yolk (control) compared to 1.75 g of egg albumen coated onto 2 g of egg yolk following the treatment with steam for 1 minute 30 seconds.

A regression line of the positive control dilution series will is made and the amount of CBUs/Kg of dried whole egg is determined based on the optical density (OD) of the positive control dilutions and the sample ODs. The activity of the anti-IL-10 antibody in the egg yolk was calculated as % survival. The results are provided in FIGS. 1-4. Using egg albumen as a coating for egg yolk cores reduced loss of anti-Il-10 antibody activity by over 70% (9.5% survival control vs. 30% survival treatment). This reduction in the loss of activity was highly statistically significant. Without being held to theory, since the albumen coating in these experiments did not dry as quickly as could be achieved in commercial coating processes, it is believed that some yolk antibody migrated to the albumen coating before drying was complete, hence, there was some loss in activity.

Example 2: Scale-Up of Coating Process

The coating of egg yolk cores with egg albumen can be scaled-up using fluidized bed coating of egg albumen onto egg yolk microparticles. Because of the speed and control of fluidized bed coating, no water removal from the egg albumen should be required.

Example 3: Experimental Protocol for Testing the Efficacy of Bioactive Molecules in Egg Yolk Cores Encapsulated with Egg Albumen An egg yolk preparation containing anti-interleukin-10 antibody will be coated with egg albumen using the protocols described herein. The goal is to determine if the albumen coated egg yolk antibody (aIL-10) is effective in preventing *Eimeria* infection.

Twenty pens of 5 broilers will be fed each to the following treatments:

1) dried egg product (negative control) added post feed pelleting;
2) aIL-10 whole dried egg product (positive control) added post feed pelleting;
3) aIL-10 yolk encapsulated in albumen added post feed pelleting (second positive control); and
4) aIL-10 yolk encapsulated in albumen add pre-feed pelleting then pelleted (test).

Chicks will be assigned to each treatment at one-day of age (20 pens of 5 chicks per treatment). On day 3 of age, half the chicks will be gavaged with a 10× vaccine dose of Advent Coccidosis Live Vaccine to induce a mild infection (10 pens of 5 chicks per treatment) while the other 10 pens of 5 chicks per treatment will receive a saline gavage. Chick body weight and feed consumption will be measured weekly and feed conversion (feed consumed/body weight gain) will be calculated. Oocysts shedding on day 7-post inoculation will be determined.

Chicks from all treatment groups not infected with *Eimeria* will have similar body weights, feed consumption, and feed conversion, and will show no oocysts shedding. In infected chicks, those fed treatment 1 (control egg product) will have a 20% reduction in weight gain and approximately 150,000 oocysts per gram excreta. Infected chicks fed the aIL-10, either coated or uncoated and fed post-pelleting will have weight gains similar to uninfected chicks, and greater than infected chicks in treatment 1, and oocysts significantly reduced (40,000 oocysts per gram of excreta) relative to treatment 1. Results from Treatments 2 and 3 will be similar to those described previously. Infected chicks fed the test treatment (treatment 4) will show one of two responses: 1) If the egg yolk coated with albumen and denature through the pelleting process does not interfere with the bioavailability of the antibody for preventing infection, the growth, feed consumption, feed conversion and oocyst counts will resemble treatments 2, and 3 for infected chicks; 2) If the denatured albumen coating the antibody due to pelleting does not release the antibody in the intestine then we will see decreased body weights, feed conversion and high oocysts shedding, similar to treat 1 for infected chicks, a support of the null hypothesis.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A composition comprising coated avian egg yolk cores comprising an egg albumen coating, wherein the avian egg yolk cores have a diameter of 100 to 1500 micrometers, wherein the ratio of dry avian egg albumen to dry avian egg yolk in the coated avian egg yolk cores is 1:10 to 10:1.

2. The composition of claim 1, wherein the dried avian egg yolk comprises a bioactive polypeptide.

3. The composition of claim 2, wherein the coated avian egg yolk cores have a dissolution profile when tested in a U.S.P. Type II dissolution apparatus at 37° C. and 50 rpm, in pH 6.8 buffer as follows: at 5 minutes greater than or equal to about 5% of the bioactive molecule is released.

4. The composition of claim 2, wherein the bioactive polypeptide comprises an enzyme, a cytokine, an antibody, a hormone, a growth factor, or a combination comprising at least one of the foregoing bioactive polypeptides.

5. The composition of claim 2, wherein the bioactive polypeptide is heat labile.

6. The composition of claim 2, wherein the bioactive polypeptide is an IgY antibody.

7. The composition of claim 6, wherein the IgY antibody was produced in the egg yolk in response to immunization of the avian with an immunogenic polypeptide.

8. The composition of claim 6, wherein the IgY antibody specifically binds the immunogenic polypeptide.

9. The composition of claim 6, wherein the IgY antibody in the coated avian egg yolk cores lose less than 50% of its bioactivity when exposed to temperatures of up to 93° C. and a steam pressure of 552 kPa for 3 minutes or less.

10. The composition of claim 1, wherein the coated avian egg yolk cores have a flow factor of greater than 4, a Hausner ratio of 1-1.25, a static angle of repose of less than 60, or a combination thereof.

11. The composition of claim 1, wherein the coated avian egg yolk cores are in the form of a feed additive composition.

12. The composition of claim 1, wherein the coated avian egg yolk cores are in the form of a feed or food composition that further comprises a basal feed or food composition.

13. A food or feed composition comprising a basal food or feed composition and the coated avian egg yolk cores of claim 1.

14. The food or feed composition of claim 13, wherein the feed composition is a pelleted feed composition.

15. The food or feed composition of claim 14, wherein the pelleted feed composition comprises chicken feed.

* * * * *